United States Patent [19]

Popelka

[11] Patent Number: 4,516,856
[45] Date of Patent: May 14, 1985

[54] OPTICAL APPARATUS FOR FLUORESCENCE POLARIZATION INSTRUMENT

[75] Inventor: Susan R. Popelka, Gurnee, Ill.

[73] Assignee: Abbott Laboratories, North Chicago, Ill.

[21] Appl. No.: 405,459

[22] Filed: Aug. 5, 1982

Related U.S. Application Data

[63] Continuation of Ser. No. 223,633, Jan. 9, 1981, abandoned.

[51] Int. Cl.³ .................... G01N 21/64; G01J 4/04
[52] U.S. Cl. .................... 356/368; 250/458.1; 250/461.1; 356/417
[58] Field of Search .............. 356/317, 318, 417, 366, 356/367, 365, 368; 250/458.1, 461.1, 461.2, 237 R

[56] References Cited

U.S. PATENT DOCUMENTS

| | | | |
|---|---|---|---|
| 4,115,699 | 9/1978 | Mizuta et al. | 250/461.2 |
| 4,160,914 | 7/1979 | Wynn | 250/237 R |
| 4,203,670 | 5/1980 | Bromberg | 356/318 |
| 4,269,511 | 5/1981 | Erwin | 356/368 |
| 4,291,230 | 9/1981 | Heiss | 250/458.1 |
| 4,293,225 | 10/1981 | Wheaton et al. | 356/417 |
| 4,295,199 | 10/1981 | Curry et al. | 250/461.2 X |

Primary Examiner—Vincent P. McGraw
Attorney, Agent, or Firm—James L. Wilcox; Dennis K. Shelton

[57] ABSTRACT

An improved optical system for a fluorescent polarization instrument including a low wattage, low intensity focused light source and a polarizer/liquid crystal combination in the excitation path focusing excitation light of alternate planes of perpendicular polarization onto a fluorescent liquid sample. Emitted light from the fluorescent sample is filtered, polarized and focused onto a photomultiplier for processing. A series of non-reflective baffles are placed around the sample to reduce reflections. Monitoring means monitor the excitation light and maintain a substantially constant intensity level focused on the sample. The low wattage, low intensity light source is provided by a 50 watt tungsten halogen projector lamp.

5 Claims, 1 Drawing Figure

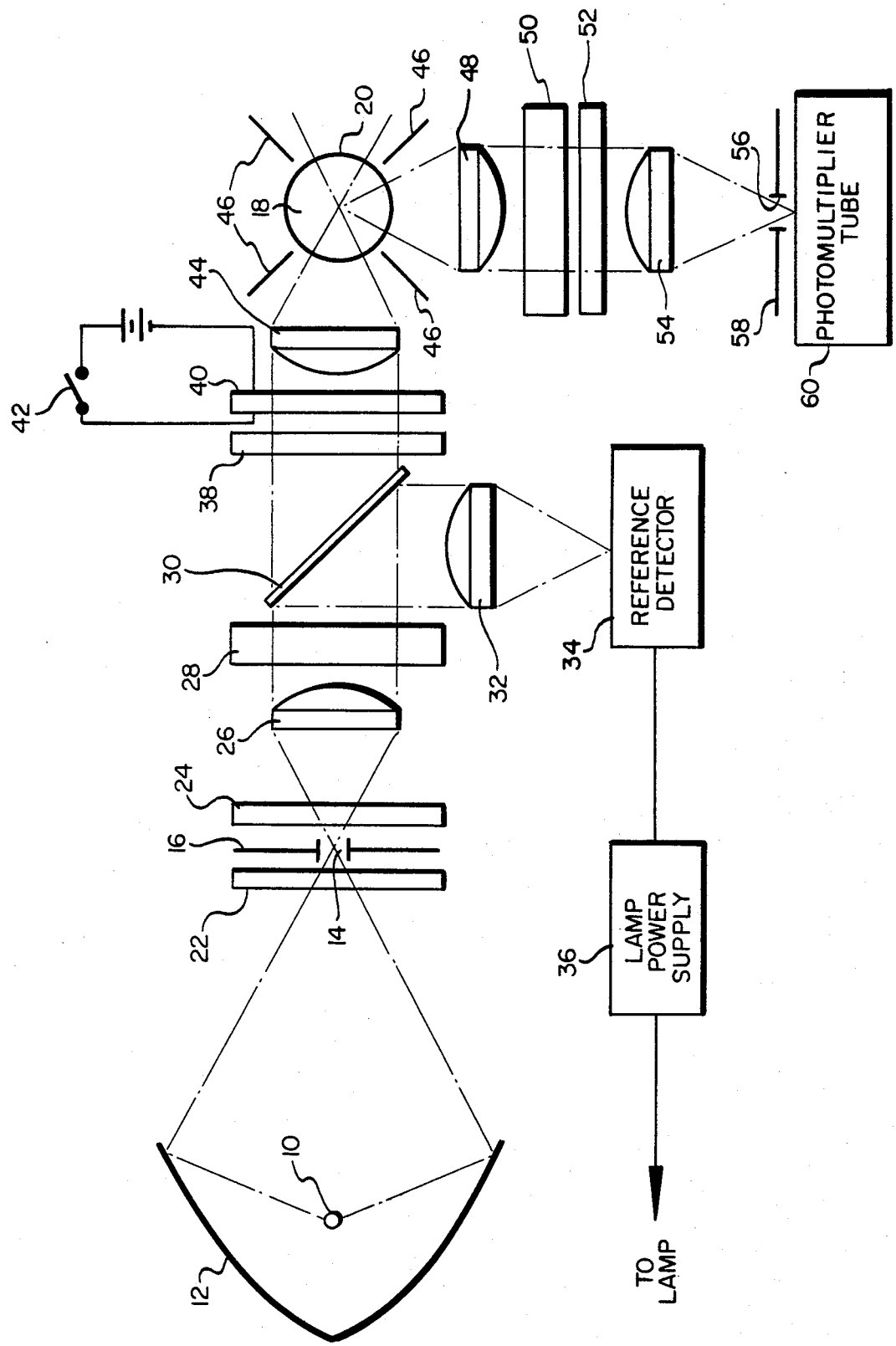

OPTICAL APPARATUS FOR FLUORESCENCE POLARIZATION INSTRUMENT

This is a continuation of application Ser. No. 223,633, filed Jan. 9, 1981, now abandoned.

This invention relates to fluorescence polarization analyzers and in particular, to an improved optical system for such an analyzer.

BACKGROUND OF THE INVENTION

Fluorescence polarization instruments and their use for clinical applications are described for instance in, "Design, Construction, and Two Applications for an Automated Flow-Cell Polarization Fluorometer with Digital Read Out: etc."; R. D. Spencer, F. D. Toledo, B. T. Williams, and N. L. Yoss; *Clinical Chemistry*, 19/8, pages 838–344 (1973). Such instruments can rapidly analyze body fluid samples labelled with a fluorescent material.

In the aforementioned article, a fluorescent polarization instrument is illustrated which includes a fluorescent sample irradiated by two beams of exciting light each linearly polarized, one vertically, the other horizontally. Alternate polarization sample excitation is provided by a sectored chopping mirror which alternately passes the vertically and horizontally polarized light to the sample. The exciting light is monochromatic corresponding to the peak of the absorption spectrum of the sample. The illuminated fluorescent sample becomes a secondary source of radiation, emitting light in a spectrum peaked at a longer wavelength than the exciting light. A vertical polarizer in the emission light path passes vertically polarized light to a photomultiplier tube for detecting the resulting emission light from the sample. The signal output of the photomultiplier tube then is analyzed to obtain the degree of polarization, P, which is determined by the expression: $I(VV) - I(HV)/I(VV) + I(HV)$, where $I(VV)$ is the measured intensity of the detected photomultiplier signal when vertically polarized light excites the sample and the vertical component of the emitted light is analyzed, and $I(HV)$ is the detected photomultiplier signal when horizontally polarized light excites the sample and the vertical component of the emitted light is analyzed.

Known instruments of such type require relatively high wattage, intense light sources such as 200–250 watt mercury or xenon gas discharge lamps in order to obtain the desired emission radiation from the sample at a signal to noise level ratio sufficient for detection and amplification by a low-noise photomultiplier tube and associated electronics. Such high wattage, bright lamps also require substantial cooling in order to maintain the integrity of the optical system. It is thus desired to provide an improved optical system for fluorescence polarization instrument which can utilize lower wattage and less intense lamps and yet provide sensitivity which is equal to or better than prior art devices.

SUMMARY OF THE INVENTION

The invention is an improved optical system for a fluorescence polarization instrument which includes a low wattage, low intensity focused light source, narrow bandwidth filter, a polarizer, and a field effect liquid crystal in the excitation path focusing excitation light onto the fluorescent liquid sample. If no electric field is applied to the liquid crystal, the liquid crystal rotates the plane of polarization of the excitation light 90 degrees, whereas if an electric field is applied to the crystal, the plane of polarization is not rotated 90 degrees. Thus, applying an electric field alternately to the liquid crystal alternately applies excitation light to the sample at polarization angles which are perpendicular to each other. Light emitted from the sample is filtered, polarized and focused onto a photomultiplier for processing.

The low wattage, low intensity light source is a 50 watt tungsten halogen lamp with a reflector focusing light onto an aperture which is sized to provide a sufficient amount of light in accordance with the quantity of liquid sample. A heat absorber is provided in the excitation path to absorb infrared radiation transmitted through the aperture from the lamp so as to minimize temperature sensitivities of the sample and of the components in the excitation path. A series of baffles, formed of thin, black metal strips, are placed around the sample so as to reduce surface reflections by the excitation light which otherwise may undesirably enter the emission path. Means are also provided for monitoring the excitation light and adjusting the lamp power supply so as to maintain a substantially constant level of excitation light intensity.

BRIEF DESCRIPTION OF THE DRAWING

FIG. 1 is a schematic block diagram illustrating an improved optical system for a fluorescence polarization instrument in accordance with the principles of the present invention.

DETAILED DESCRIPTION

Referring now to FIG. 1, there is illustrated a low wattage, low intensity tungsten halogen lamp 10 which includes a reflector 12 for focusing light from the lamp onto an aperture 14 formed in a light shielding element 16. Reflector 12 is in a form of an elliptical mirror. Light shielding element 16 comprises a thin metal plate approximately ¾ mm thick having a black, non-reflecting surface on both sides thereof. Aperture 14 is about 3 mm in diameter which gives sufficient amount of light to conform to about a one ml liquid fluorescent sample 18 contained in a round test tube 20. Lamp 10 and elliptical mirror 12 can be provided by a conventional 50 watt tungsten halogen projector lamp readily available as a purchased item.

On either side of the apertured light shielding element 16, there is provided a heat reflector or infrared suppressor 22 and a heat absorber 24 for respectively reflecting and absorbing infrared radiation transmitted from the lamp, and thus minimizing any temperature sensitivities of the sample and components in the oxication path. The heat reflector may be provided by a dichroic film multi-layer reflector. The heat absorber can be provided by a readily available type BG-38 absorber colored glass, such as available from Corion Corporation.

A plano-convex lens 26 collimates the light from the aperture 14. The collimated light then passes through a narrow bandwidth filter 28 corresponding nearly to the absorption peak of the fluorescent sample. A transparent glass beam splitter 30 reflects about 4% of the incident light onto a plano-convex lens 32 which in turn focuses the light onto a reference detector 34. The output of the reference detector is used to monitor and adjust the intensity of the lamp through lamp power supply 36. The lamp filament is adjusted through lamp power supply 36 in accordance with the detected reference signal level from reference detector 34 so as to maintain a constant level of excitation light intensity directed to sample 18. Beam splitter 30 may be provided by a microscope cover glass which is transparent and transmits 96% while reflecting about 4% of the incident light.

Light which is transmitted through the beam splitter is then incident upon a polarizer 38 and liquid crystal 40 combination which functions as a plane of polarization rotator. Polarizer 38 has a fixed plane of polarization which for example may be the horizontal plane, H. Liquid crystal 40 is of the transmissive shutter type rotating light impinging on it by 90 degrees when no electric field is applied to the crystal, and providing no rotation of the polarization plane of incident light when an electric field is applied to the crystal. Selective application of electric field to the crystal 40 is indicated schematically in the drawing by closing switch 42 which will apply a voltage and thus an electric field to the crystal.

Thus, in the embodiment shown in the drawing, the horizontal polarizer/liquid crystal combination is used to alternately excite fluorescent sample 18 with vertical and horizontal polarized light by initially leaving switch 42 open so that the liquid crystal rotates the light impinging on it by 90 degrees, and thus the sample is excited by vertical light, and thereafter closing switch 42, so that no rotation occurs and horizontal light excites the sample. The polarized, collimated, excitation light is then focused by a plano-convex lens 44 into the center of fluorescent sample 18 in round test tube 20. Stray light may be introduced into the emission optics by reflections at the air-to-glass and glass-to-liquid interfaces of the sample-filled culture tube 20. In order to minimize this effect, the lamp filament 10 is focused at the center of the culture tube 20, thus allowing all rays (incident and reflected) to enter and exit the culture tube normal to its surface. Since the emission optics to be described hereinafter images the central region of the fluorescent sample 18 with optimal efficiency, focusing the lamp filament to the center of the culture tube increased the system efficiency and thus maximizes the throughput of the entire system. It is the throughput of the present system which permits a relatively low wattage, low intensity tungsten halogen lamp to be utilized as a light source. Reference may be made to U.S. Pat. No. 4,195,932, S. R. Popelka, assigned to the same assignee as here, wherein there is discussed an absorption spectrophotometer in which light is focused to the center of a round test tube to greatly reduce errors due to test tube deviation.

The polarizer 38 and liquid crystal 40 combination in the excitation light channel is an important aspect of the present invention. The use of electro-optical devices in the emission channel has been proposed by others. However, it has been found that inherent rotational errors obtained through the liquid crystal being subjected to a spectrum of polarization components in the emission channel result in measured polarization values which are not accurate. In such proposals, it has been suggested that the inherent rotational errors when employing a liquid crystal in the emission channel can be significantly reduced by utilizing appropriate initial reference data to compensate for the later measured polarization rotational errors. However, the suggested compensation requires additional data storage components, and a time consuming initial calibration procedure to derive the compensation data.

In contrast, these errors experienced in the prior art are eliminated in the present invention by placing the liquid crystal in the excitation channel and by utilizing a fixed plane polarizer preceeding the liquid crystal so that only a single plane of polarization is incident onto the liquid crystal. Therefore, the liquid crystal rotates the single plane of polarization component without significant error.

A series of baffles 46 comprising thin plastic or metal strips having black, substantially non-reflecting surfaces are located around sample 18 so as to prevent gross reflections of excitation light by the test tube 20 and surrounding areas from entering the emission optics as stray light. As illustrated in the drawings, the excitation optics channel and the emission optics channel are perpendicular to each other, so as to reduce the possibility of excitation light undesirably entering the emission channel. Since the amount of emitted radiation from the fluorescent sample is very low, it is desired to reduce as much as possible the presence of any stray excitation light in the emission channel. It has been found that without the baffles 46 bordering the fluorescent sample, the stray excitation light contributes appreciably to the measured polarization valve in both increasing the absolute value and worsening the reproducibility, whereas, when utilizing the baffles, these undesired effects are substantially eliminated.

Sample 18 may contain, for instance, a body fluid to which has been added a substance tagged with a fluorescent label such as sodium fluorescein. The labelled biological molecules are then excited by the incident light from the excitation light channel to emit light at a longer wavelength. A plano-convex lens 48 collimates the emitted light which then traverses a wide bandwidth emission interference filter 50 corresponding nearly to the emission peak of the fluorescent sample, and a vertical polarizer 52 having a fixed plane of vertical polarization. The collimated, vertically polarized, emission light is then focused by a plano-convex lens 54 onto an aperture 56 in a substantially non-reflecting light shielding element 58 at the input to a photomultiplier tube 60 for further processing in accordance with known techniques. The emission aperture 56 is 3.0 by 8.0 mm which conforms to the light viewing volume in sample container 20.

In a contructed prototype embodiment of the present invention, wherein the sample was labelled with sodium fluorescien, the excitation filter 28 is centered at a wavelength of 485 nm, with a half power bandwidth of 10 nm. Emission filter 50 has a center wavelength of 540 nm with a half power bandwidth of 30 nm. All of the lenses shown in the drawing have an anti-reflective coating, with 16.7 mm focal length; 15 mm diameter; 14.4 mm back focal length; and an index of refraction of 1.785. Sensitivity on the order of $10^{-11}$ molar of sodium fluoresein was obtained for the constructed prototype.

The foregoing detailed description has been given for clearness of understanding only, and no unnecessary limitations should be understood therefrom, as modifications will be obvious to those skilled in the art.

What is claimed is:

1. Optical apparatus for a fluorescence polarization analyzer wherein a fluorescent liquid sample is irradiated with excitation light and radiates an emission light from which the polarization, P, is determined in accordance with the expression: $I(Z)-I(Y)/I(Z)+I(Y)$, where $I(Z)$ is the measured intensity of one polarization component of the emitted light at a first polarization angle when the liquid sample is irradiated with polarized excitation light at the first polarization angle, and where I(Y) is the measured intensity of the polarization component of emitted light at the first polarization angle when the liquid sample is irradiated with polarized excitation light at a second polarization angle perpendicular with respect to said first polarization angle, said optical apparatus comprising:

a sample tube for containing said liquid sample, said sample tube having a substantially circular peripheral cross-sectional configuration;

a focused light source for irradiating said liquid sample with excitation light focused substantially at the center of said sample;

said focussed light source comprising a relatively low wattage, low intensity tungsten halogen lamp;

a narrow bandwith filter intermediate said focused light source and said sample for passing excitation light corresponding substantially to the absorption band of the fluorescent sample;

a first polarizer intermediate said narrow bandwidth filter and said sample, said polarizer having a fixed plane of polarization at said first polarization angle;

a field effect liquid crystal intermediate said polarizer and said sample, including means for alternately applying an electric field to said liquid crystal to alternately apply excitation light polarized at the first or second polarization angles to said liquid sample;

a photomultiplier detector including an input aperture restricting the emission light viewed by said photomultiplier;

baffle means adjacent the sample tube substantially preventing reflections of excitation light from entering the path of said emission light to said photomultiplier input aperture;

emission light focusing lenses intermediate said sample and said photomultiplier for focusing emitted light to said photomultiplier input aperture;

a second polarizer intermediate said sample and said photomultiplier having a fixed plane of polarization at said first polarization angle; and a wide bandwidth filter intermediate said sample and said photomultiplier for passing emitted light corresponding substantially to the emission band of the fluorescent sample.

2. Optical apparatus according to claim 1, wherein said first and second polarizers comprise vertical polarizers.

3. Optical apparatus according to claim 2, wherein said focused light source further includes:

a reflector for said tungsten halogen lamp;

a light shielding element having an aperture receiving excitation light reflected said lamp; and excitation light focusing lenses intermediate the aperture and the sample for focusing excitation light at the center of the sample.

4. Optical apparatus according to claim 3, including an infrared absorbing element intermediate said aperture and said excitation light focusing lenses.

5. Optical apparatus according to claim 4, including excitation light monitoring means for monitoring the intensity of said excitation light to maintain the light intensity substantially constant.

* * * * *